United States Patent
Fonfe et al.

(10) Patent No.: US 10,703,715 B2
(45) Date of Patent: Jul. 7, 2020

(54) PROCESS FOR THE PREPARATION OF AN ALKANESULFONIC ACID

(71) Applicant: Evonik Operations GmbH, Essen (DE)

(72) Inventors: Benjamin Fonfe, Frankfurt (DE); Chiu Kee Cheung, Alzenau (DE); Ali Hartwig, Gruendau (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/121,979

(22) Filed: Sep. 5, 2018

(65) Prior Publication Data

US 2019/0071394 A1    Mar. 7, 2019

(30) Foreign Application Priority Data

Sep. 6, 2017  (EP) .................... 17189551

(51) Int. Cl.
*C07C 303/16* (2006.01)
*B01J 19/00* (2006.01)
*B01J 19/18* (2006.01)

(52) U.S. Cl.
CPC .......... *C07C 303/16* (2013.01); *B01J 19/002* (2013.01); *B01J 19/0066* (2013.01); *B01J 19/18* (2013.01); *B01J 19/1862* (2013.01); *B01J 2219/002* (2013.01); *B01J 2219/00033* (2013.01); *B01J 2219/00065* (2013.01); *B01J 2219/00094* (2013.01); *B01J 2219/00101* (2013.01); *B01J 2219/00103* (2013.01); *B01J 2219/00162* (2013.01); *B01J 2219/00182* (2013.01); *B01J 2219/00186* (2013.01); *B01J 2219/00211* (2013.01); *B01J 2219/00263* (2013.01); *B01J 2219/00779* (2013.01); *B01J 2219/2474* (2013.01)

(58) Field of Classification Search
CPC ..... C07C 51/60; C07C 303/16; C07C 309/04; B01J 19/002; B01J 19/0066; B01J 19/18; B01J 19/1862; B01J 2219/00033; B01J 2219/00065; B01J 2219/00094; B01J 2219/00101; B01J 2219/00103; B01J 2219/00162; B01J 2219/00182; B01J 2219/00186; B01J 2219/002; B01J 2219/00211; B01J 2219/00263; B01J 2219/00779; B01J 2219/2474
See application file for complete search history.

(56) References Cited

U.S. PATENT DOCUMENTS

| | | | |
|---|---|---|---|
| 2,727,920 A * | 12/1955 | Johnson | C07C 303/16 562/118 |
| 3,428,671 A | 2/1969 | Toland et al. | |
| 4,900,480 A * | 2/1990 | Litz | B01F 3/04531 261/123 |
| 5,211,924 A | 5/1993 | Lee et al. | |
| 6,124,497 A | 9/2000 | Chen | |
| 8,273,923 B2 * | 9/2012 | Borremans | C07C 29/62 568/841 |
| 2002/0172629 A1 * | 11/2002 | Jahn | B01J 19/0046 422/187 |
| 2003/0088129 A1 | 5/2003 | Marshall, Jr. et al. | |
| 2004/0186316 A1 | 9/2004 | Choudary et al. | |
| 2014/0051890 A1 * | 2/2014 | Finkeldei | C07C 319/16 568/41 |
| 2016/0068380 A1 * | 3/2016 | Rege | B67D 1/0808 222/23 |

FOREIGN PATENT DOCUMENTS

| | | |
|---|---|---|
| EP | 2 596 861 A1 | 5/2013 |
| PL | 226044 B1 | 6/2017 |
| WO | WO 2009/023515 A2 | 2/2009 |

OTHER PUBLICATIONS

MSDS (Methyl mercaptan, published Jun. 2013) (Year: 2013).*
Safety (Chapter Twelve Safety in Chemical Reaction Engineering, Modeling of Chemical Kinetics and Reactor Design, pp. 910-1033, published 2001) (Year: 2001).*
Boiler Supplies (published Oct. 2015) (Year: 2015).*
Extended European Search Report dated Oct. 24, 2018 in Patent Application No. 18192500.9, 7 pages.
Extended European Search Report dated Feb. 22, 2018 in Patent Application No. 17189551.9.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to a process for the preparation of an alkanesulfonic acid by oxidation of a sulfur containing starting compound with an oxygen containing fluid, wherein the sulfur containing starting compound is provided in a reaction system, comprising a reaction vessel (1) with an expansion vessel (2) on its top, wherein the reaction vessel and the expansion vessel are connected to allow a flow of a fluid stream from the reaction vessel into the expansion vessel.

18 Claims, 3 Drawing Sheets

PROCESS FOR THE PREPARATION OF AN ALKANESULFONIC ACID

The present invention relates to a process for the preparation of an alkanesulfonic acid by oxidation of a sulfur containing starting compound.

Alkanesulfonic acids can be prepared by oxidation of alkyl mercaptans, dialkyl disulfides and/or dialkyl polysulfides to the corresponding alkanesulfonic acids. Several oxidizing agents are described in the literature for this oxidation reaction.

For example, the use of molecular bromine as oxidizing agent in the preparation of an alkanesulfonic acid from alkyl mercaptan and/or dialkyl disulfide, as taught in WO 98/34914 A1, impairs the purity of the thus prepared alkanesulfonic acid. In this process, hydrogen bromide is initially oxidized with oxygen in the presence of catalytic amounts of nitric acid, or with nitric acid as oxidizing agent, to give molecular bromine. The oxides of nitrogen that form in this reaction are regenerated with oxygen and water to give nitric acid, which is returned to the process step of the oxidation of hydrogen bromide to molecular bromine. Thereafter, using the molecular bromine obtained in this way, the starting material, i.e. an alkyl mercaptan and/or dialkyl disulfide, is oxidized to the corresponding alkanesulfonic acid. As a result of the use of the molecular bromine, the alkanesulfonic acids prepared by the method of WO 98/34914 A1 always contain halogen. However, in the fabrication of circuit boards, which is one of the most important fields of applications of alkanesulfonic acids, such as methanesulfonic acid, the presence of halogens must be fundamentally avoided. Consequently, the alkanesulfonic acids obtained by the method of WO 98/34914 A1 are not suitable for this important application.

It is also known to use hydrogen peroxide as oxidizing agent for the preparation of alkanesulfonic acids from alkylmercaptans or dialkyl disulfides. However, this reaction only runs without difficulties when carboxylic acids are present. It is therefore believed that the percarboxylic acid, which is formed from the carboxylic acid and the hydrogen peroxide, constitutes the real active oxidizing agent. It is particularly disadvantageous that this process results in a mixture of alkanesulfonic acids with carboxylic acids and percarboxylic acids from which the alkanesulfonic acids can often be separated in pure form only with difficulty. Thus, a cost- and energy-intensive recovery of the alkanesulfonic acids is necessary, which makes this process economically unattractive. A further cost driver is the use of hydrogen peroxide, which is a rather expensive oxidizing agent. Another disadvantage is that one mole of water is formed per one mole of reacted hydrogen peroxide and thus, considerable amounts of water are formed. Moreover, this reaction by-product cannot be converted again to the oxidizing agent but must be separated from the desired alkanesulfonic acid by cost- and energy-intensive distillation processes.

U.S. Pat. No. 4,239,696 discloses an alternative process for the oxidation of alkylmercaptans and dialkyl disulfides with hydrogen peroxide. In this process alkylmercaptans or dialkyl disulfides are oxidized with hydrogen peroxide in a liquid reaction medium, which contains from 1 to 35% of an alkanesulfonic acid, based on the amount of alkylmercaptans or dialkyl disulfides, and is free of carboxylic and percarboxylic acids. The rather long reaction time of three hours and the employment of the expensive oxidizing agent hydrogen peroxide are significant disadvantages, which make this process rather unattractive from an economic point of view. More importantly, the U.S. Pat. No. 4,239,696 teaches to carry out the reaction in two steps when the process is performed as a continuous process, where the first step is carried out at temperatures of up to 90° C. and the second step at temperatures between 100° C. and 110° C. However, alkanesulfonic acids such as methanesulfonic acid are corrosive at these temperatures and thus, would lead to severe corrosion phenomena, which makes this process also unattractive from a safety-related point of view.

U.S. Pat. No. 2,727,920 discloses a process for the single-stage oxidation of alkyl mercaptans with aqueous nitric acid and oxygen to the corresponding alkanesulfonic acids. In this process, however, the aqueous nitric acid is introduced in a multi-molar excess, in other words superstoichiometrically, in relation to the mercaptan to be converted. As a consequence considerable amounts of water and nitrogen oxides must be separated from the resulting alkanesulfonic acid. However, increasing the ratio of mercaptan to nitric acid is not an option, because according to U.S. Pat. No. 2,727,920 even small amounts of alkyl mercaptan react with such vigor that the metering of larger amounts of alkyl mercaptan to the nitric acid is out of the question, owing to the attendant explosion hazard. With this process, therefore, only low space-time yields are achievable. The process of U.S. Pat. No. 2,727,920, consequently, is not suited for the industrial production of alkanesulfonic acids.

WO 00/31027 A1 discloses a process for the preparation of alkanesulfonic acids by oxidizing alkyl mercaptans, dialkyl disulfides and/or dialkyl polysulfides with nitric acid at temperatures of from 50° C. to 150° C. As a result of the large fraction of nitric acid in the reaction mixture, considerable amounts of water are introduced into the reaction, and must subsequently be separated, with high energy consumption and high cost, from the desired product. Another disadvantage of this process lies in the formation of large amounts of nitrogen oxides, which are detrimental to health and a hazard to the environment, and of which dinitrogen oxide, $N_2O$, is also classified as a greenhouse gas. In order to avoid the release of these nitrogen oxides measures must be taken, which are likewise high in cost and energy, and which therefore make the process of WO 00/31027 A1 generally unattractive.

The published Chinese patent application CN-A 101648892 discloses the preparation of alkanesulfonic acids by oxidation of a dialkyl disulfide using air and nitric acid. In this process, nitric acid is always in excess in relation to the dialkyl disulfide to be oxidized. The decomposition of considerable amounts of nitric acid results in discoloration of the product. To remove the color, therefore, the product mixture must be admixed with a DeNOx catalyst. Moreover, the use of large amounts of nitric acid in this process also has the disadvantage that the large quantities of water introduced must be separated off again by highly energy-intensive distillation processes.

Alternatively, suitable sulfur containing starting compounds can also be oxidized with oxygen as the main oxidizing agent and in the optional presence of a catalyst, as in the process of the U.S. Pat. No. 2,505,910. This document discloses another process for the preparation of alkanesulfonic acids by oxidizing alkyl mercaptans with oxygen in the presence of catalytic amounts of nitric acid and small amounts of water. In that process, a solution comprising an alkyl mercaptan and an oxide of nitrogen as catalyst is gassed with air. Before oxygen is absorbed in this solution, a mercaptan nitrogen oxide complex is formed. However, when the oxidation of the mercaptan in this complex begins, this occurs, according to U.S. Pat. No. 2,727,920, with almost explosive vigor. The examples of U.S. Pat. No.

2,505,910 also describe a vigorous release of $NO_2$ when the process is carried out, a phenomenon which also gives rise to severe foaming within the reactor. The process of U.S. Pat. No. 2,505,910, therefore, does not allow a simple and safe procedure and is consequently not suitable for the large-scale production of alkanesulfonic acids.

Accordingly, the use of oxygen as the main oxidizing agent in the preparation of alkanesulfonic acids from suitable sulfur containing starting compounds, indeed, has advantages over the use of other oxidizing agents such as nitric acid, molecular bromine or hydrogen peroxide. However, oxidation reactions usually proceed under the release of reaction heat. This is of particular relevance with respect to sulfur containing starting compounds having a low boiling point, such as alkyl mercaptans or dialkyl disulfides, because the amount of the reaction heat which is released over the course of the oxidation reaction can lead to a vaporization of the sulfur containing starting compound. The thus obtained vapor of the sulfur containing starting compound can form a gas mixture with the oxygen. However, the formation of a gas mixture of sulfur containing starting compounds with oxygen is always dangerous, because such gas mixtures can be prone to explosions.

It is therefore a problem to be solved to provide a process for the preparation of alkanesulfonic acids, which avoids the formation of explosive gas mixtures or at least significantly reduces the dangers associated with the formation of explosive gas mixtures.

According to the present invention the problem is solved in that the preparation is performed in a reaction system comprising a reaction vessel (1) and an expansion vessel (2). The expansion vessel is placed on top of the reaction vessel and both vessels are connected via connection line (3). Said connection allows the flow of a fluid stream from the reaction vessel into the expansion vessel.

Depending on their specific composition, mixtures of oxygen or air with volatile sulfur containing starting compounds can be explosion-prone. The expansion vessel according to the present invention thus allows a gas phase, in particular a gaseous mixture of a volatile sulfur containing starting compound, such as the sulfur containing starting compound, with oxygen or air, which is formed during the conduct of reaction taking place in the reaction vessel, to expand into the expansion vessel. The use of the expansion vessel according to the present invention therefore also provides for the separation and/or isolation of explosion-prone mixtures of air or oxygen with volatile sulfur containing sulfur containing starting compounds from the large liquid phase in the reaction vessel, which mainly comprises the specific sulfur containing starting sulfur containing starting compound to be oxidized. In this way the risk of an explosion in the reaction vessel is significantly reduced compared to the standard procedure of performing the oxidation reaction of an sulfur containing starting compound in a typical reaction vessel without the expansion vessel according to the present invention. Even if an explosion did nevertheless occur in the expansion vessel, the explosion would be limited to the expansion vessel so that its impact would be comparably small. Thus, the expansion vessel acts like a sacrificial vessel in favor of the reaction vessel.

An object of the present invention is therefore a process for the preparation of an alkanesulfonic acid by oxidation of a sulfur containing starting compound with an oxygen containing fluid, wherein the sulfur containing starting compound is provided in a reaction system, comprising a reaction vessel (1) with an expansion vessel (2) on its top, wherein the reaction vessel and the expansion vessel are connected to allow a flow of a fluid stream from the reaction vessel into the expansion vessel.

By comparison, the reaction systems typically used in the preparation of alkanesulfonic acids by oxidation of suitable sulfur containing starting compound do not have the expansion vessel according to the present invention. Thus, these systems constitute only a reaction vessel. A disadvantage of the use of such systems in the preparation of alkanesulfonic acids by oxidation is that they have a much larger continuous gas phase above the said gas-liquid phase and thus pose a greater danger in terms of explosion potential.

In the context of the present invention the term fluid is used to denote any type of fluid, such as a gas, a liquid, a gaseous mixture, a liquid mixture or a mixture of a gas and a liquid.

The oxygen containing fluid can be air, oxygen, pure oxygen, or air enriched with oxygen and thus a content of more than 21 volume-percent of oxygen. Said oxygen containing fluid is introduced into a liquid phase comprising the sulfur containing starting compound by means of an immersion pipe or a frit, wherein the immersion pipe or the frit is placed at the bottom or close to the bottom of the reaction vessel.

In the context of the present invention the term expansion vessel is used to denote any type of vessel which is suitable for the separation of a gas and liquid phase in a fluid stream such that a continuous gas phase is formed above the said gas-liquid phase. In addition, the thus formed continuous and stable gas phase permits the use of a suitable pressure controlling valve, known to the expert skilled in the art, to regulate the reaction pressure within the reaction system to the desired level.

Preferably, the sulfur containing starting compound of the process according to the present invention is an alkyl mercaptan, a dialkyl disulfide and/or a dialkyl polysulfide. In particular, the alkyl radical of the aforementioned sulfur containing starting compounds is always identical, when two or more different types of sulfur containing starting compounds are used in the process according to the present invention, e.g. an alkyl mercaptan together with a dialkyl disulfide or a dialkyl disulfide together with a dialkyl polysulfide. It is further preferred that said alkyl radical comprises from 1 to 4 carbon atoms. Preferably, the sulfur containing starting compound of the process according to the present invention is a methyl mercaptan, dimethyl disulfide and/or a dimethyl polysulfide, since the thus obtained methansulfonic acid is the commercially most relevant alkanesulfonic acid.

It is beneficial to keep any gas phase within the reaction system as small as possible. One option to achieve this condition is to flood the reaction vessel with a liquid phase. Specifically, the reaction vessel is flooded with a liquid phase comprising the sulfur containing starting compound, which is to be oxidized to the corresponding alkanesulfonic acid. This at least significantly reduces the danger that a volatile sulfur containing starting compound could form an explosion prone gas mixture with oxygen. If nevertheless a gas mixture of a volatile sulfur containing starting compound and oxygen was formed, its accumulation in the reaction vessel is avoided. Rather, the formed gas mixture of a volatile sulfur containing starting compound and oxygen will flow from the reaction vessel into the expansion vessel and the same applies to any further gas mixtures to be formed of the volatile sulfur containing starting compound and oxygen.

In another embodiment of the process according to the present invention the reaction vessel is completely flooded with a liquid phase.

In principle, the process according to the present invention is not subject to any limitation regarding the specific mode of carrying out the respective process. Therefore, the process according to the present invention can be carried out in batch, continuous or semi-continuous mode. In context of the present invention the terms batch and continuous are used as known to the person skilled in the art. In the context of the present invention the term semi-continuous mode is used to denote a process that is carried in alternating sections of batch and continuous mode. Preferably, the process according to the present invention is carried out in continuous mode, because it is the most efficient mode for the industrial scale production of chemicals. When the process is operated continuously or semi-continuously, to maintain a constant inventory within it, it is necessary to withdraw the same liquid volume out of the it as that of the reactants entering the reaction system of the process according to the present invention. In principle, the liquid volume withdrawn from the reaction system is the reaction product or reaction product mixture, i.e. either the alkanesulfonic acid to be prepared as such or the alkanesulfonic acid comprising product mixture. The liquid phase entering the reaction system is in principle the reactants comprising mixture, i.e. the one or more sulfur containing starting compound optionally in a suitable solvent, preferably in the alkanesulfonic acid to be prepared as solvent.

In one embodiment of the process according to the present invention the liquid volume withdrawn from the reaction system equals the volume of the liquid phase entering the reaction system, when the process is operated in continuous or semi-continuous mode.

The formation and/or accumulation of gas mixtures during the preparation of the alkanesulfonic acid may lead to an increase of the pressure within the reaction system. However, any gas mixtures formed this process will flow from the reaction vessel into the expansion vessel, where they form a continuous gas phase. Any increase in reaction pressure can therefore regulated by means of pressure controlling valve, preferably placed in the expansion vessel, to a desired value.

In one embodiment of the process according to the present invention the reaction pressure within the reaction system is regulated by means of a pressure controlling valve.

In order to keep the impacts of a possible explosion as small as possible, the volume of the expansion vessel should always be smaller than the volume of the reaction vessel.

In a further embodiment of the process according to the present invention the volume of the expansion vessel is smaller than the volume of the reaction vessel.

For a combustion or an explosion to take place, the three corners of the combustion or explosion triangle have to be present, i.e. oxygen, sulfur containing starlings and an ignition source. Since oxygen is typically omnipresent in the oxidation of an sulfur containing starting compound on an industrial scale, the safety concept of a reactor or a reaction system for the oxidation of an sulfur containing starting compound should ensure that during the operation of the reactor the concentration of an sulfur containing starting compound in the gas phase is always below the lower explosion limit. In the context of the present invention the term lower explosion limit is used according to the general knowledge of the person skilled in the art and denotes the lowest concentration (percentage) of a gas or a vapor in air or oxygen capable of producing a flash of fire in the presence of an ignition source, for example a flame, heat, arc, or static electricity. At a concentration in air or oxygen lower than the lower explosion limit, gas mixtures are "too lean" to burn. The specific value of said lower explosion limit depends on the individual sulfur containing starting compounds and their vapor pressure, their concentration in the gas phase, the oxygen concentration in the gas phase and the additional presence of other compounds in the gas phase, in particular of those other compounds which lead to a decrease of the lower explosion limit. The safety concept of a reactor or a reaction system for the oxidation of an sulfur containing starting compound should also ensure that—in addition to the operation of the reactor—the concentration of an sulfur containing starting compound is also below the lower explosion limit during start-up, shutdown and any operational failures. To ensure that the concentration of an sulfur containing starting compound, with respect to the present invention the sulfur containing starting compound, in the gas phase is always below the lower explosion limit, the reaction system according to the present is equipped with both an online analysis device to continuously measure the gas phase concentration of an sulfur containing starting compound within the expansion vessel and an offline analysis method to periodically measure the gas phase concentration of an sulfur containing starting compound within the expansion vessel. The online analysis serves as the primary operational safeguard and if the measured online sulfur containing starting concentrations in the gas phase approaches a pre-determined lower explosion limit then a signal from the online analysis will instigate first an alarm and if remedial action cannot rectify the high concentration then an automatic safe shutdown of the reactor will be undertaken by the digital control system (DCS) used to operate the reaction system. The preferred method for the online gas analysis of the sulfur containing starting compounds is Fourier transform infrared (FTIR) spectroscopy. Since the offline probes are only taken intermittently, there is an inherent time lag before process perturbations are registered with offline analytics. Therefore, the offline analysis of the gas phase serves only as a safety device in case of problems with the FTIR; an offline gas chromatograph (GC) is the preferred offline analysis method used to monitor the gas phase.

In one embodiment of the process according to the present invention the concentration of an sulfur containing starting compound in the gas phase is monitored by means of an online analysis device and/or an offline analysis device.

Said online analysis device, preferably Fourier transform infrared (FTIR) spectrometer, and said offline analysis device, preferably gas chromatograph (GC), are connected to the reaction system according to the present invention by means of one or more of the lines (8, 9, 10, 11 and/or 12) in the expansion vessel.

In a preferred embodiment of the process according to the present invention the concentration of an sulfur containing starting compound in the gas phase is monitored online by means of an Fourier transform infrared spectrometer and/or offline by means of a gas chromatograph.

According to its liquid vapor equilibrium, the gas phase concentration of an sulfur containing starting compound is always related to its liquid phase concentration. As such, it is possible to add an extra layer of safety to the reaction system by using an online analysis device to continuously measure the liquid phase concentration of relevant sulfur containing starting compounds in the reaction vessel to ensure that the liquid phase concentration corresponding to the lower gas explosion limit is not exceeded. The preferred method for the online liquid analysis of the sulfur containing starting compounds is near infrared (NIR) spectroscopy. Similar to the FTIR, the NIR signal is connected directly to the DCS and at pre-determined concentrations of the measured sulfur containing starting compounds at first alarms are sounded and if remedial action do not decrease the sulfur containing starting concentration, then an automatic safe shutdown of the reactor is instigated.

Accordingly, in another embodiment of the process according to the present invention the concentration of an sulfur containing starting compound in the liquid phase is monitored by means of an online analysis device.

Said online analysis device, preferably near infrared (NIR) spectrometer, is connected to the reaction system according to the present invention at or after the liquid outlet of the reaction vessel to minimize the presence of entrained gas bubbles within the liquid phase. Gas bubbles are detrimental to the NIR measurement method and it is preferable to install a degasser upstream of the NIR spectrometer to separate any gas from the liquid stream before the analysis.

In a prefer embodiment of the process according to the present invention the concentration of an sulfur containing starting compound in the liquid phase is monitored by means of a near infrared spectrometer.

Because of the design of the reaction system used in the process, any formation and accumulation of an explosive gas phase comprising an sulfur containing starting compound and oxygen can only happen in the expansion vessel. In order to avoid the formation and accumulation of an explosive gas phase comprising an sulfur containing starting compound and oxygen, it is preferred to regularly monitor the concentration of an sulfur containing starting compound in the gas phase within the expansion vessel. Preferably, an online Fourier transform infrared (FTIR) spectrometer and a gas chromatograph (GC) are used to monitor the gas phase concentration of an sulfur containing starting compound. As a means of precaution, the liquid concentration of an sulfur containing starting compound is also measured online in or after the reaction vessel with a near infrared (NIR) spectrometer to validate and to complement the other two analysis methods.

Thus, in a further embodiment of the process according to the present invention the concentration of an sulfur containing starting compound in the gas phase within the expansion vessel and/or the concentration of an sulfur containing starting compound in the liquid phase are regularly monitored.

When the concentration of an sulfur containing starting compound in the gas phase of the expansion vessel reaches a threshold value the oxidation reaction is stopped. Preferably, the oxidation reaction is stopped by terminating the feeding of the oxygen containing fluid stream into the oxidation reaction, in other words the feeding of the oxygen containing fluid stream into the reaction vessel is stopped. Preferably, the threshold value for the concentration of an sulfur containing starting compound is below the lower explosion limit for a gas phase comprising the sulfur containing starting compound and a specific oxygen content or at a specific pressure of oxygen or air.

In a further embodiment of the process according to the present invention the oxidation of the sulfur containing starting compound is stopped when the concentration of an sulfur containing starting compound in the gas phase of the expansion vessel approaches the lower explosion limit.

Static electricity can be a source of ignition in a reaction system for the oxidation of an sulfur containing starting compound. The reaction system according to the present invention therefore involves a grounding of all parts in order to avoid any ignition of the gas phase due to static electricity or even the build-up of any static electricity.

Therefore, in another embodiment of the reaction system according to the present invention the vessels, the piping and the equipment parts are grounded to avoid any static electricity.

Said grounded equipment parts are in particular the NIR spectrometer, the FTIR spectrometer and the gas chromatograph.

In order to provide for safe operating conditions, it is of particular relevance to monitor the course of an oxidation reaction, which is performed in the reaction system according to the present invention, for example the rapid onset or the vigorous course of the reaction. Both the rapid onset and the vigorous course of a reaction but also the targeted decay of the reaction can easily be monitored with a thermometer or a similar temperature measurement device known to the person skilled in the art. Therefore, the expansion tank according to the present invention is preferably equipped with a thermometer. Said thermometer can be either introduced into the expansion vessel through a point at the top of the expansion vessel, in particular the lines (8, 9, 10 and/or 11), and/or through a point at and/or close to the lower end of the expansion vessel, such as the line (12). Furthermore, the temperature can also be monitored directly in the reactor vessel at and/or after the liquid outlet. Therefore, the reaction vessel and/or the expansion vessel of the reaction system used in the process according to the present invention is/are equipped with a thermometer.

According to the present invention, the liquid volume withdrawn from the reaction system equals the volume of the liquid phase entering the reaction system to maintain a constant inventory within it, when the reaction system is operated continuously or semi-continuously. However, the reaction vessel is fully flooded with liquid and gas bubbles and therefore, it is necessary to measure the level of liquid within the expansion vessel to enable the automatic control of the liquid inventory within the reaction system. Since the excess air or oxygen from the reactor vessel exits as a gas-liquid stream into the expansion vessel, this can cause strong fluctuations of the liquid level within the expansion level, which can cause problems in the accurate measurement of the liquid level.

This problem is solved when the measuring point is not placed in the expansion vessel itself but in a riser tube (13) which runs from a lower point to a higher point of the reaction system. In particular, the riser tube runs from the connection line (3) connecting the reaction with the expansion vessel to a point in the upper half of the expansion vessel. For example, the riser tube (13) is connected via a connection line (14) to a flow-through point in the upper half of the expansion vessel and via a connection line (15) to a flow-through point in the connection line (3). Alternatively, the riser tube runs from the bottom of the expansion tank to a point in the upper half of the expansion vessel. Both the expansion vessel and the riser tube form a system of communicating tubes within the reaction system according to the present invention. As a consequence the level of a liquid phase which enters the expansion vessel always has the same height as in the riser tube. Further, the riser tube branches off only a part of the liquid stream, which enters the expansion vessel. Therefore, the liquid level of the liquid phase, which enters the riser tube, has a rather quiescent surface compared to the liquid stream entering the expansion vessel. Consequently, it is possible to monitor the inflow and the extent of inflow of a liquid phase into the expansion vessel very reliably. The liquid level in the expansion tank or in the riser tube is monitored by means of a liquid level indicator which is introduced into the riser tube via its top. There are many methods, such as floats, radar, guided radar, capacitive, hydrostatic, and radiation measurements, which can be used to measure the liquid level within the expansion tank or the riser tube. It is preferred to use the radar technique, and it is especially preferred to use a guided radar device to measure the liquid level.

In a further embodiment of the process according to the present invention the liquid level in the expansion vessel is monitored by means of a liquid level indicator, wherein said liquid level indicator is placed in a riser tube (13) which runs from the bottom of the expansion vessel or from a line (3) connecting the expansion tank with the reaction vessel to a point in the upper half of the reaction vessel.

Additionally, anything happening in the expansion vessel can also be monitored by means of one or more inspection windows (17) in the expansion vessel.

In principle, the process according to the present invention is not limited to a specific reaction vessel. Rather, the reaction vessel can be for example a reactor run in continuous, semi-continuous or batch mode. Preference is given to a reactor run in continuous mode, for example one or more continuously stirred tank reactors (CSTR), such as a series of continuously stirred tank reactors, e.g. several continuously stirred tank reactors in series or several continuously stirred tank reactors in parallel. In the case that the reaction system of the process comprises more than one continuously stirred tank reactor, every single reactor is equipped with the expansion tank according to the present invention.

In one embodiment of the process according to the present invention the reaction system comprises at least one continuously stirred tank reactor.

It can be either desired or undesired that a temperature gradient from the reaction vessel to the expansion vessel be established. Therefore, it can be either suitable to cool or to heat the inner volume of the expansion tank. Preferably, both the reaction vessel and the expansion tank of the reaction system in the process according to the present invention are each equipped with a heat exchange apparatus such as a jacket (4, 5) for the accommodation of a heat exchanger medium. However, the heat exchange equipment is not limited to the exemplary jacket, heating coils and other forms of equipment known to those skilled in the art can also be used for the reaction system.

In the process according to the present invention the sulfur containing starting compound is either present as a liquid as such or it is present in solution with a suitable solvent. Preferably, said solvent is the alkanesulfonic acid to be prepared. This has the advantage that there is no need for an additional purification step to remove a solvent from the product. The oxygen containing fluid is introduced are introduced into the liquid phase with the sulfur containing starting compound to be oxidized by means of an immersion pipe, a frit or any other devices suitable for introducing and distributing gases in liquid phases. The immersion pipe, the frit or the other type of gas distribution device is preferably placed at the bottom or close to the bottom of the reaction vessel. Even though this design already provides for a good dispersion of gas bubbles in the liquid phase, it is still far from an optimum mass transfer from the gas to the liquid phase. Rather, it is preferred that a radial pumping or radial working stirrer, such as a Smith Turbine, is placed in the bottom of the reaction vessel above the injection point of air or oxygen into the liquid phase. The radial pumping or radial working stirrer disperses the stream or big bubbles of air or oxygen, which was injected into the liquid phase, into tiny bubbles and then distributes them evenly across the diameter of the reaction vessel. It is further preferred that at least one axial pumping or axial working stirrer, such as a Viskoprop stirrer, is placed above the radial pumping or radial working stirrer in order to mix the gas bubbles with the liquid phase along the height of the reaction vessel and as such the typical constant concentration profile of a continuously stirred tank reactor is achieved. The number of axial pumping or axial working stirrers depends on the height of the reaction vessel. Both the radial pumping or radial working stirrer and the at least one axial pumping or axial working stirrer are connected to the same stirrer shaft. Said shaft protrudes into the reaction vessel from the bottom upwards to prevent the accumulation of oxygen at the top of the stirrer shaft and in particular at the top of the reaction vessel, which could otherwise lead to a build-up of an explosive gas atmosphere when the concentration of volatile sulfur containing starting compounds reaches the relevant lower explosion limit.

In a further embodiment of the process according to the present invention the sulfur containing starting compound is mixed with the oxygen containing fluid by means of a bottom radial pumping or bottom radial working stirrer (6) and at least one top axial pumping or top axial working stirrer (7).

Usually, the extension of the stirrer shaft goes through the bottom of the reaction vessel and is directly connected to its drive below the reaction vessel. This, however, requires a very good sealing of the stirrer system when either oxidizing and/or corrosive substances are used or prepared in the oxidation reaction, which is carried out in the reaction vessel. Accordingly, this design is also susceptible to any leakages. Furthermore, the use of sealing media, such as lubricants, can lead to a contamination of the reaction system, which may require a work and cost intensive purification of the reaction product. It is therefore preferred, that a magnet coupled drive is used for the stirrer of the reaction vessel. This does not only minimize the leaking potential of the stirrer system but it also eliminates the need of any sealing media such as lubricants and thus, avoids the danger of contaminating the reaction system.

Therefore, in a preferred embodiment of the process according to the present invention the stirrer of the reaction vessel is equipped with a magnet coupled drive.

The present invention is further described by the following items:
1. A reaction system comprising a reaction vessel (1) with an expansion vessel (2) on its top, wherein the reaction vessel and expansion vessel are connected to allow a flow of a fluid stream from the reaction vessel into the expansion vessel, and the reaction vessel is equipped with a bottom radial pumping or bottom radial working stirred (6) and at least one top axial pumping or top axial working stirrer (7), wherein the stirrer of the reaction vessel is equipped with a magnet coupled drive.
2. The reaction system according to item 1, wherein the reaction system is equipped with a pressure controlling valve to regulate the reaction pressure within the reaction system.
3. The reaction system according to item 1 or 2, wherein the volume of the expansion vessel is smaller than the volume of the reaction vessel.
4. The reaction system according to any of items 1 to 3, wherein the reaction system is equipped with an online analysis device and/or an offline analysis device suitable for monitoring the concentration of a sulfur containing starting compound in the gas phase.

5. The reaction system according to item 4, wherein the online device is a Fourier transform infrared spectrometer, and the offline analysis device is a gas chromatograph.
6. The reaction system according to any of items 1 to 5, wherein the reaction system is equipped with an online analysis device suitable for monitoring the concentration of a sulfur containing starting compound in the liquid phase.
7. The reaction system according to item 6, wherein the online analysis device is a near infrared spectrometer.
8. The reaction system according to any of items 1 to 7, wherein the vessels, the piping, and the equipments parts of the reaction system are ground to avoid any static electricity.
9. The reaction system according to item 8, wherein the near infrared spectrometer, the Fourier transform infrared spectrometer and the gas chromatograph are grounded.
10. The reaction system according to any of items 1 to 9, wherein the reaction system comprises a liquid level indicator.
11. The reaction system according to item 10, wherein the liquid level indicator is placed in a riser tube (13) which runs from the bottom of the expansion tank or from a line (3) connecting the expansion tank with the reaction vessel to a point in the upper half of the reaction vessel.
12. The reaction system according to any of items 1 to 11, wherein the reaction system comprises at least one continuously stirred tank reactor.
13. Use of a reaction system according to any of items 1 to 12 in the oxidation of an organic compound.

LIST OF REFERENCE NUMERALS

Figure 1:
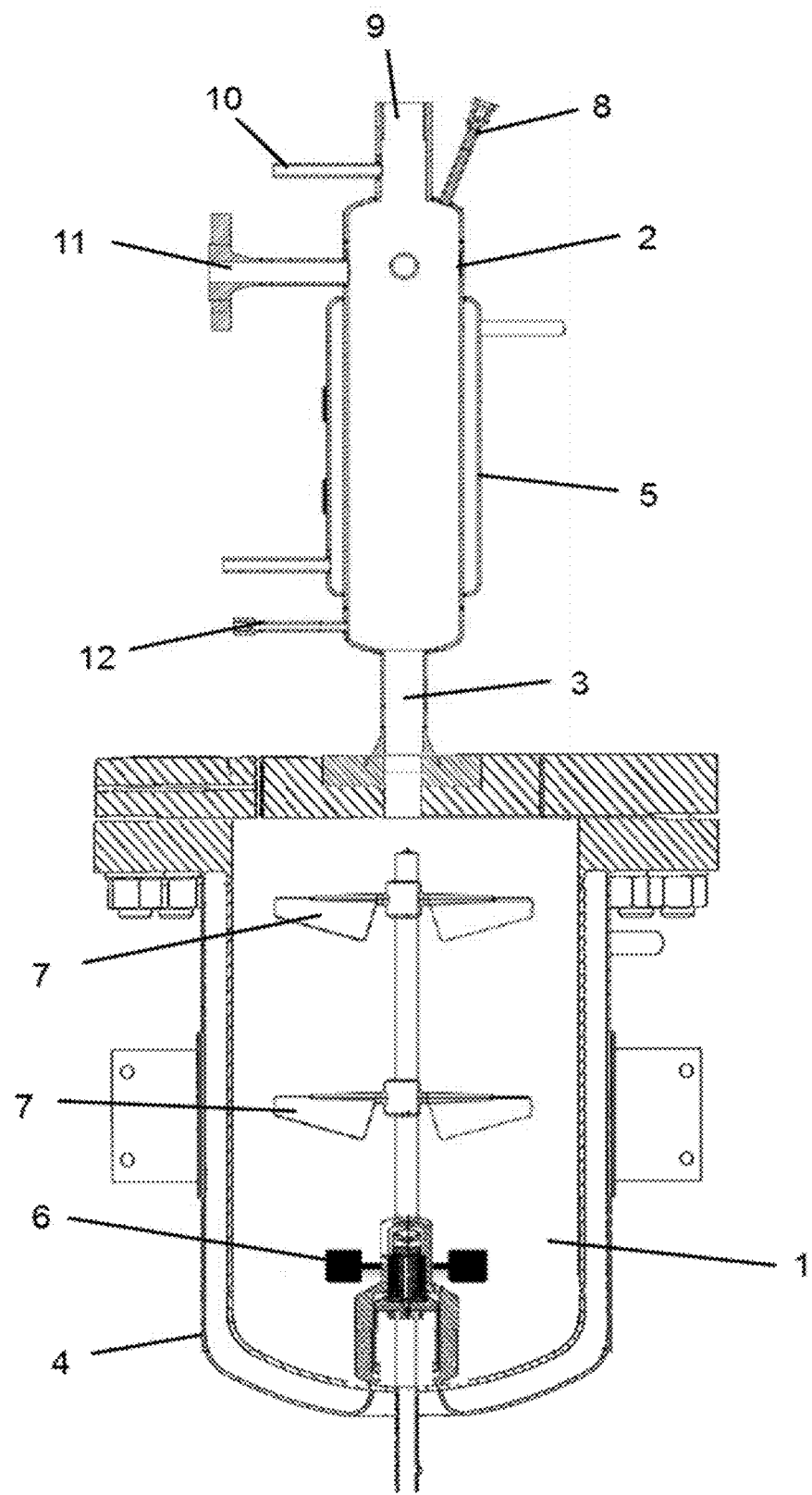
FIG. 1 is a cross-sectional view of the reaction system according to the present invention.
Figure 2:
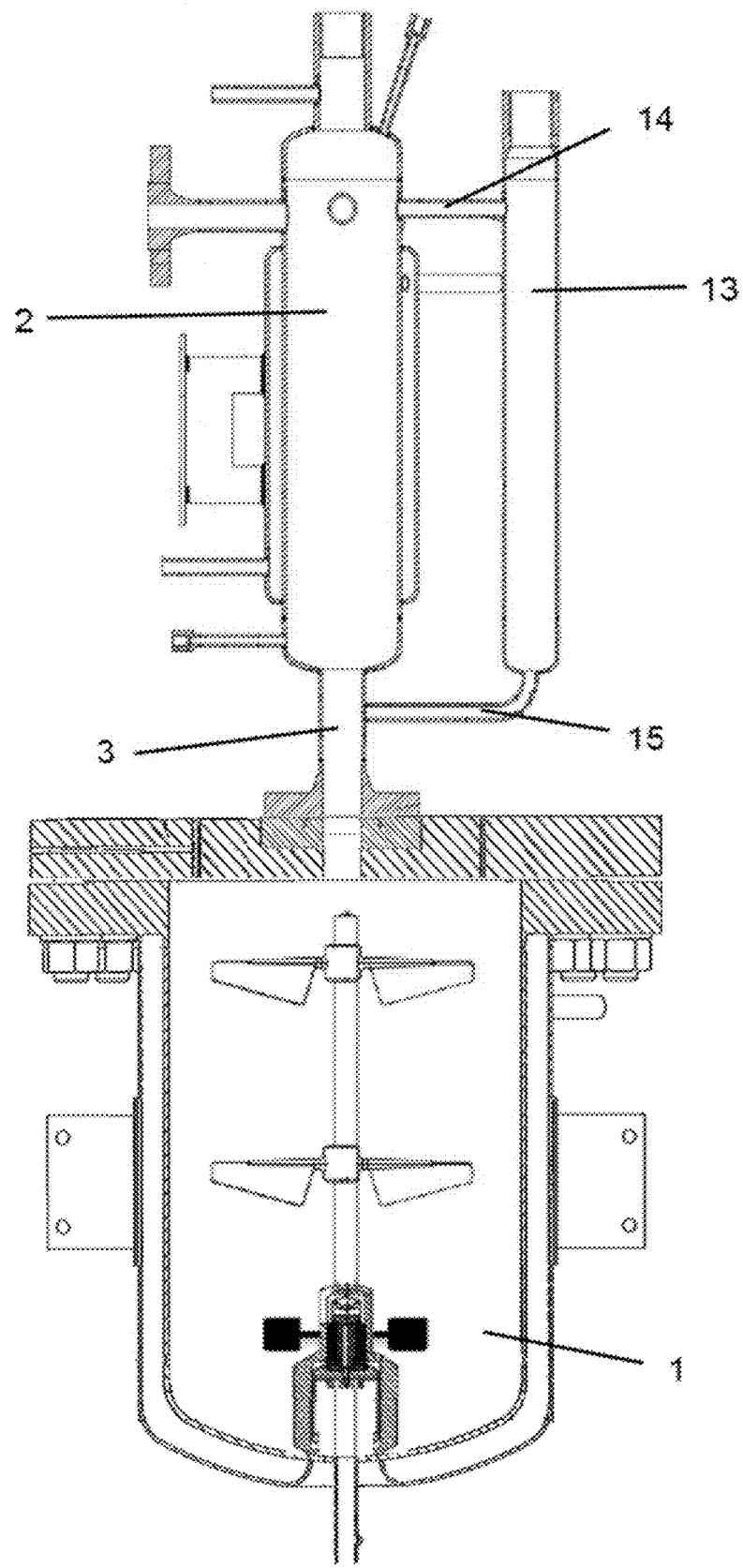
FIG. 2 is a cross-sectional view of an embodiment of the reaction system according to the present invention with a riser tube.
Figure 3:
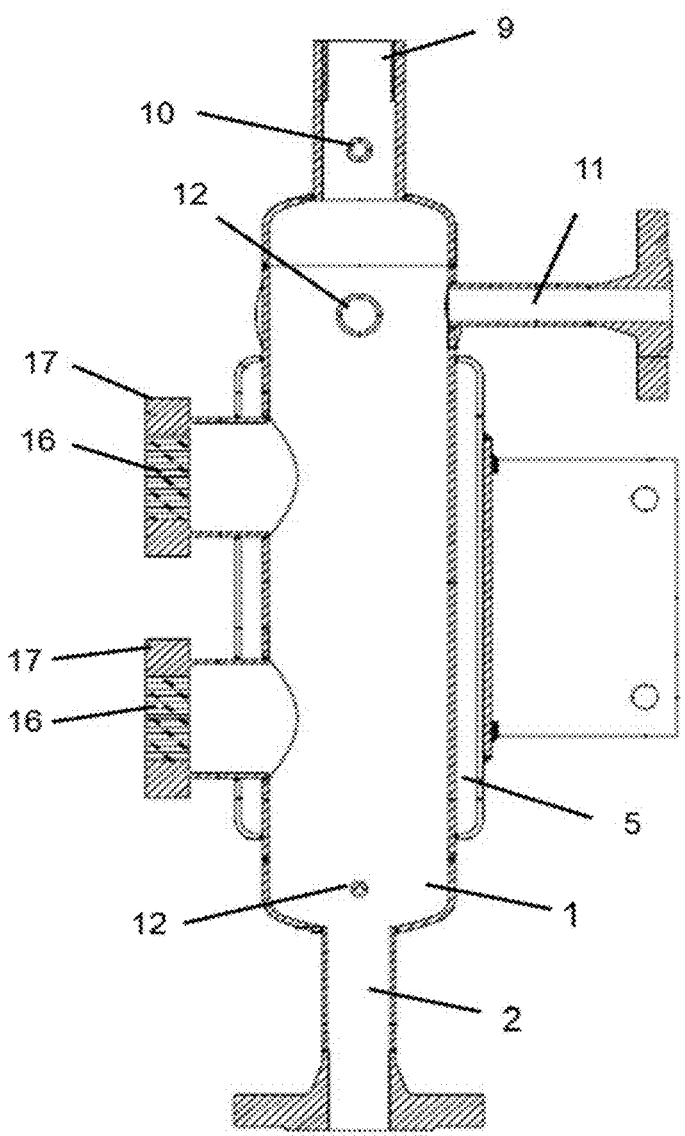
FIG. 3 is a cross-sectional view of the expansion vessel.

The reference numbers in the FIGS. 1 to 3 denote the following items:
1 reaction vessel
2 expansion vessel
3 connection line
4 jacket of the reaction vessel
5 jacket of the expansion vessel
6 bottom axial working stirrer
7 top radial working stirrer
8 line for sample extraction, introducing thermometer
9 line for sample extraction, introducing thermometer
10 line for sample extraction, introducing thermometer
11 line for sample extraction, introducing thermometer
12 line for sample extraction, introducing thermometer
13 riser tube
14 connection line between riser tube (13) and expansion vessel (2)
15 connection line between riser tube (13) and connection line (3)
16 inspection windows
17 casings for inspection windows (16)

The invention claimed is:

1. A process for preparing an alkanesulfonic acid by oxidation of a starting compound comprising sulfur with a fluid comprising oxygen, the method comprising:
providing the starting compound in a reaction system,
wherein the reaction system comprises a reaction vessel and an expansion vessel on top of the reaction vessel, wherein the reaction vessel and the expansion vessel are connected to allow a flow of a fluid stream from the reaction vessel into the expansion vessel.
2. The process according to claim 1, wherein the reaction vessel is completely flooded with a liquid phase.
3. The process according to claim 2, wherein a liquid volume withdrawn from the reaction system equals a volume of the liquid phase entering the reaction system, when the process is operated in continuous or semi-continuous mode.
4. The process according to claim 1, wherein a reaction pressure within the reaction system is regulated by means of a pressure controlling valve.
5. The process according to claim 1, wherein a volume of the expansion vessel is smaller than a volume of the reaction vessel.
6. The process according to claim 1, wherein a concentration of the starting compound in a gas phase is monitored by means of an online analysis device, an offline analysis device, or both.
7. The process according to claim 6, wherein the concentration of the starting compound in the gas phase is monitored online by means of an Fourier transform infrared spectrometer, offline by means of a gas chromatograph, or both.
8. The process according to claim 1, wherein a concentration of the starting compound in a liquid phase is monitored by means of an online analysis device.
9. The process according to claim 8, wherein the concentration of the starting compound in the liquid phase is monitored online by means of a near infrared spectrometer.
10. The process according to claim 6, wherein the concentration of the starting compound in the gas phase within the expansion vessel, a concentration of the starting compound in a liquid phase, or both, are regularly monitored.
11. The process according to claim 6, wherein the oxidation of the starting compound is stopped when the concentration of the starting compound in the gas phase approaches or reaches a lower explosion limit.
12. The process according to claim 1, wherein a liquid level in the expansion vessel is monitored by means of a liquid level indicator placed in a riser tube which runs from a bottom of the expansion vessel or from a line connecting the expansion vessel with the reaction vessel to a point in an upper half of the reaction vessel.
13. The process according to claim 1, wherein the reaction system comprises at least one continuously stirred tank reactor.
14. The process according to claim 1, wherein the starting compound is mixed with the fluid by means of a bottom radial pumping or bottom radial working stirrer and at least one top axial pumping or top axial working stirrer.
15. The process according to claim 14, wherein the stirrer of the reaction vessel is equipped with a magnet coupled drive.
16. The process according to claim 2, wherein the liquid phase comprises the alkanesulfonic acid.
17. The process according to claim 1, wherein the process is carried out in a continuous mode.
18. The process according to claim 1, wherein in the providing, a single type of sulfur-containing compound is provided in the reaction system.

* * * * *